United States Patent
Hamachi et al.

(10) Patent No.: US 12,378,487 B2
(45) Date of Patent: Aug. 5, 2025

(54) METHOD FOR PRODUCING ORGANIC SUBSTANCE AND APPARATUS FOR PRODUCING ORGANIC SUBSTANCE

(71) Applicant: SEKISUI CHEMICAL CO., LTD., Osaka (JP)

(72) Inventors: Kokoro Hamachi, Tokyo (JP); Satoshi Shimizu, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 317 days.

(21) Appl. No.: 17/794,388

(22) PCT Filed: Jan. 21, 2021

(86) PCT No.: PCT/JP2021/002028
§ 371 (c)(1),
(2) Date: Jul. 21, 2022

(87) PCT Pub. No.: WO2021/149765
PCT Pub. Date: Jul. 29, 2021

(65) Prior Publication Data
US 2023/0050575 A1    Feb. 16, 2023

(30) Foreign Application Priority Data
Jan. 23, 2020 (JP) .................................. 2020-009372

(51) Int. Cl.
*C07C 27/28*    (2006.01)
*C10K 1/06*    (2006.01)

(52) U.S. Cl.
CPC ................ *C10K 1/06* (2013.01); *C07C 27/28* (2013.01)

(58) Field of Classification Search
CPC ...... B01D 1/16; B01D 17/0214; B01D 3/143; C07C 27/28; C10K 1/06; C10K 1/10; C12P 7/065; C12P 7/08
See application file for complete search history.

(56) References Cited

U.S. PATENT DOCUMENTS 6,463,864 B2    10/2002    Yamamoto et al.
9,410,095 B2    8/2016    Zhang et al.
(Continued)

FOREIGN PATENT DOCUMENTS

CN    102803497    11/2012
CN    108722173    11/2018
(Continued)

OTHER PUBLICATIONS

International Search Report (ISR) issued Mar. 2, 2021 in International (PCT) Application No. PCT/JP2021/002028.
(Continued)

*Primary Examiner* — Sharon Pregler
(74) *Attorney, Agent, or Firm* — WENDEROTH, LIND & PONACK, L.L.P.

(57) ABSTRACT

Provided are a method for producing an organic substance and an apparatus for producing an organic substance that are capable of efficiently cooling a synthesis gas and converting the synthesis gas to an organic substance at a high conversion efficiency using a microbial catalyst. A method for producing an organic substance includes a step of passing a synthesis gas G1 discharged from a gasifier 2 through a heat exchanger 20 to cool the synthesis gas G1, a step of passing the synthesis gas G1 cooled with the heat exchanger 20 through a gas cooling tower 21 to cool the synthesis gas G1 with water sprayed in the gas cooling tower 21 and a step of bringing the synthesis gas G1 that has passed through at least the heat exchanger 20 and the gas cooling tower 21 into
(Continued)

contact with a microbial catalyst to generate an organic substance.

9 Claims, 1 Drawing Sheet

(56) References Cited

U.S. PATENT DOCUMENTS

| | | | |
|---|---|---|---|
| 10,577,577 | B2 | 3/2020 | Satou et al. |
| 10,865,425 | B2 | 12/2020 | Fujimori et al. |
| 2002/0033123 | A1 | 3/2002 | Yamamoto et al. |
| 2008/0299650 | A1 | 12/2008 | Krieg |
| 2009/0038316 | A1 | 2/2009 | Pearson |
| 2010/0051875 | A1 | 3/2010 | Chornet et al. |
| 2010/0298450 | A1* | 11/2010 | Datta ............... C01B 3/382 518/702 |
| 2012/0052541 | A1 | 3/2012 | Oakley |
| 2012/0142522 | A1 | 6/2012 | Pearson |
| 2013/0137151 | A1 | 5/2013 | Tobey et al. |
| 2014/0131622 | A1 | 5/2014 | Winter et al. |
| 2014/0305043 | A1 | 10/2014 | Zhang et al. |
| 2016/0222340 | A1 | 8/2016 | Satou et al. |
| 2019/0256874 | A1 | 8/2019 | Fujimori et al. |
| 2020/0048665 | A1* | 2/2020 | Simpson ............... C12M 29/26 |
| 2021/0054418 | A1 | 2/2021 | Nishiyama et al. |
| 2021/0054419 | A1 | 2/2021 | Fujimori et al. |

FOREIGN PATENT DOCUMENTS

| | | |
|---|---|---|
| JP | 2001-314725 | 11/2001 |
| JP | 2003-225642 | 8/2003 |
| JP | 3558039 | 8/2004 |
| JP | 2004-249203 | 9/2004 |
| JP | 2006-104339 | 4/2006 |
| JP | 2007-045857 | 2/2007 |
| JP | 2007-237135 | 9/2007 |
| JP | 2009-298825 | 12/2009 |
| JP | 2014-125577 | 7/2014 |
| JP | 2014-227450 | 12/2014 |
| JP | 2015-510522 | 4/2015 |
| JP | 2017-216997 | 12/2017 |
| JP | 2018-58042 | 4/2018 |
| JP | 2019-88240 | 6/2019 |
| JP | 2019-167424 | 10/2019 |
| WO | 2015/037710 | 3/2019 |
| WO | 2019/188730 | 10/2019 |

OTHER PUBLICATIONS

Nie, H.H., "Production of Sulphite Pulp," Chemical Pulp Technology, vol. 1, Light Industry Press, pp. 221-228, May 1960 (with partial English translation (3 pages)).

International Search Report (ISR) issued Mar. 2, 2021 in International (PCT) Application No. PCT/JP2021/002027.

* cited by examiner

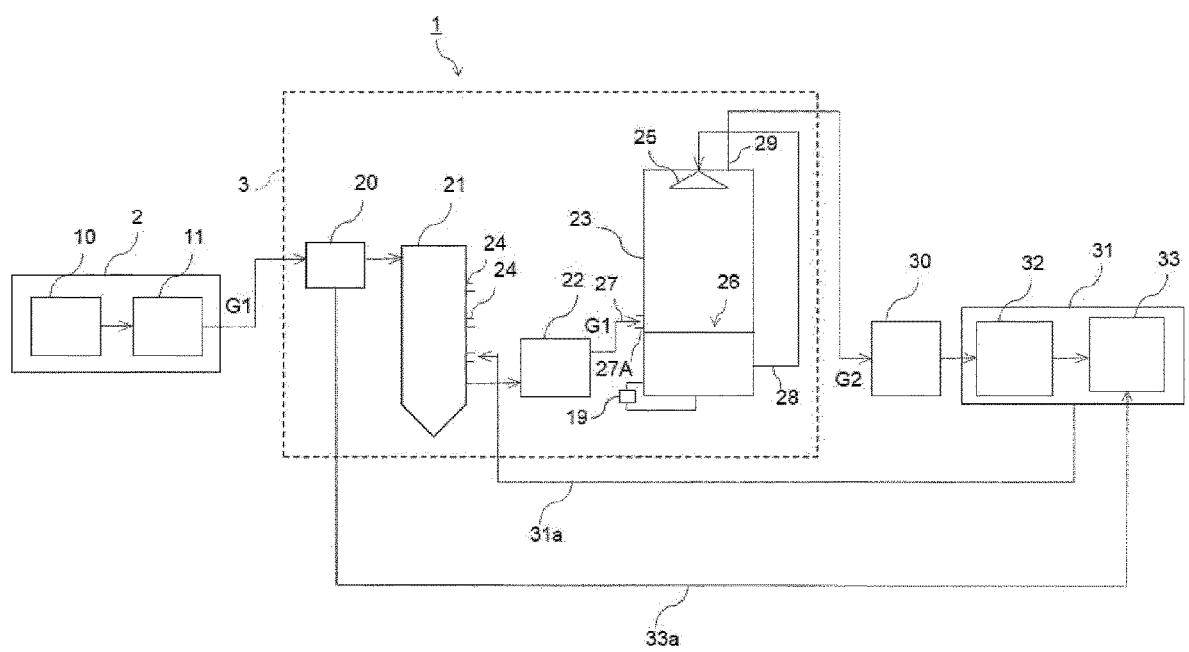

METHOD FOR PRODUCING ORGANIC SUBSTANCE AND APPARATUS FOR PRODUCING ORGANIC SUBSTANCE

TECHNICAL FIELD

The present invention relates to a method for producing organic substance in which an organic substance is produced using a synthesis gas as a raw material and an apparatus for producing an organic substance in which an organic substance is produced using a synthesis gas as a raw material.

BACKGROUND ART

Techniques that thermally decompose a variety of wastes such as industrial waste and general waste to generate a gas in a gasification furnace and then reform the generated gas to obtain a synthesis gas in a reforming furnace are broadly known. The obtained synthesis gas is combusted as it is and used for power generation or the like or is used for power generation or the like after heat is recovered with a boiler or the like as necessary.

In addition, recently, attempts have been underway to use a synthesis gas as a chemical synthesis raw material, and, for example, attempts have been underway to convert a synthesis gas to an organic substance such as ethanol using a microbial catalyst (for example, refer to PTL 1).

Synthesis gases obtained in the gasification furnace and the reforming furnace contain a large amount of an impurity such as a tar component, and it is difficult to use the synthesis gases as they are for power generation and chemical synthesis, and thus it is ordinary to purify the gases. It is known that synthesis gas is cooled as appropriate during the purification of the gas. As means for cooling a synthesis gas, means for cooling a synthesis gas using the evaporation heat of water by spraying the water to a gas flow is ordinarily used. However, the temperature of a synthesis gas obtained in a gasification furnace and a reforming furnace is high, a large amount of water is required to cool the synthesis gas by a spray of water, and a large amount of drainage water is generated. Therefore, as a method for cooling a synthesis gas, methods including means other than a spray of water have been proposed (for example, refer to PTL 2 to 4).

PTL 2 discloses that biomass is gasified at a high temperature and a normal pressure, the gasified synthesis gas is introduced into a rapid cooling tower from a gasification furnace through a water cooling pipe, and a crude synthesis gas is cooled with sprayed water in a cooling tower.

PTL3 discloses a method including a cooling step of a synthesis gas generated by gasification with an indirect heat exchanger, a tar removal step, a cooling step with a tar removal device and a cooling step by water spray spraying in a spray tower.

PTL4 discloses a method including a cooling step of cooling a synthesis gas with a first heat exchanger and spraying cooling water to the synthesis gas cooled with the first heat exchanger in a spray tower.

CITATION LIST

Patent Literature

PTL1: International Publication No. WO 2015/037710
PTL2: JP 2015-510522 A
PTL3: JP 2009-298825 A
PTL4: JP 2014-227450 A

SUMMARY OF INVENTION

Technical Problem

Incidentally, in a case where a synthesis gas is used as, for example, an organic synthesis raw material, it is necessary to strictly control the temperature in some cases. For example, in a case where a synthesis gas is converted to an organic substance such as ethanol using a microbial catalyst, it is necessary to cool the synthesis gas to a temperature of 40° C. or lower to prevent the death of the microbial catalyst.

However, in the case of using a synthesis gas for power generation or the like, strict temperature control is not required. Therefore, even when the conventional methods for purifying a synthesis gas described in PTL 2 to 4 are applied to the case of using a microbial catalyst as they are, it is difficult to synthesize organic substances at a high conversion efficiency.

In addition, in the conventional cooling of a synthesis gas, ordinarily, nitrogen or an air is blown in many cases; however, in the case of using a microbial catalyst, when nitrogen or an air is mixed into the synthesis gas, the conversion efficiency of an organic substance decreases.

Therefore, an objective of the present invention is to provide a method for producing an organic substance and an apparatus for producing an organic substance that are capable of efficiently cooling a synthesis gas and converting the synthesis gas to an organic substance at a high conversion efficiency using a microbial catalyst.

Solution to Problem

As a result of intensive studies, the present inventors found that the above-described objective can be achieved by cooling a synthesis gas with a heat exchanger, cooling the synthesis gas cooled with the heat exchanger with water sprayed in a gas cooling tower and bringing the cooled synthesis gas into contact with a microbial catalyst to generate an organic substance and completed the present invention below.

That is, the present invention provides [1] to [18] below.

[1] A method for producing an organic substance including a step of passing a synthesis gas discharged from a gasifier through a heat exchanger to cool the synthesis gas, a step of passing the synthesis gas cooled with the heat exchanger through a gas cooling tower to cool the synthesis gas with water sprayed in the gas cooling tower, and a step of bringing the synthesis gas that has passed through at least the heat exchanger and the gas cooling tower into contact with a microbial catalyst to generate an organic substance.

[2] The method for producing an organic substance according to [1], in which a temperature of the synthesis gas discharged from the gasifier is 900° C. or higher.

[3] The method for producing an organic substance according to [1] or [2], in which the synthesis gas is cooled to a temperature of 200° C. or higher and 300° C. or lower in the heat exchanger.

[4] The method for producing an organic substance according to any one of [1] to [3], further including a step of passing the synthesis gas cooled in the gas cooling tower through a filtration-type dust collector, in which the synthesis gas that has passed through at least the heat exchanger, the gas cooling tower and the filtration-type dust collector is brought into contact with a microbial catalyst to generate an organic substance.

[5] The method for producing an organic substance according to any one of [1] to [4], further including a step of passing the synthesis gas cooled in the gas cooling tower through a water scrubber, in which the synthesis gas that has passed through at least the heat exchanger, the gas cooling tower and the water scrubber is brought into contact with a microbial catalyst to generate an organic substance.

[6] The method for producing an organic substance according to [5], in which the synthesis gas that has passed through the heat exchanger, the gas cooling tower, the filtration-type dust collector and the water scrubber in this order is brought into contact with a microbial catalyst to generate an organic substance.

[7] The method for producing an organic substance according to [5] or [6], in which the synthesis gas is cooled to 40° C. or lower in the water scrubber.

[8] The method for producing an organic substance according to any one of [1] to [7], further including a step of distilling the organic substance, in which a heat energy obtained from the synthesis gas with the heat exchanger is used for distillation.

[9] The method for producing an organic substance according to any one of [1] to [8], in which the organic substance contains ethanol.

[10] An apparatus for producing an organic substance including a gasifier that generates a synthesis gas, a heat exchanger through which the synthesis gas discharged from the gasifier is passed to be cooled, a gas cooling tower through which the synthesis gas cooled in the heat exchanger is passed to be cooled by water spray, and an organic substance generation portion that brings the synthesis gas that has passed through at least the heat exchanger and the gas cooling tower into contact with a microbial catalyst to generate an organic substance.

[11] The apparatus for producing an organic substance according to [10], in which a temperature of the synthesis gas discharged from the gasifier is 900° C. or higher.

[12] The apparatus for producing an organic substance according to [10] or [11], in which the synthesis gas is cooled to a temperature of 200° C. or higher and 300° C. or lower in the heat exchanger.

[13] The apparatus for producing an organic substance according to any one of [10] to [12], further including a filtration-type dust collector which is disposed in a post-stage of the gas cooling tower and through which the synthesis gas cooled in the gas cooling tower is passed, in which the organic substance generation portion brings the synthesis gas that has passed through at least the heat exchanger, the gas cooling tower and the filtration-type dust collector into contact with the microbial catalyst to generate an organic substance.

[14] The apparatus for producing an organic substance according to any one of [10] to [13], further including a water scrubber which is disposed in a post-stage of the gas cooling tower and through which the synthesis gas cooled in the gas cooling tower is passed, in which the organic substance generation portion brings the synthesis gas that has passed through at least the heat exchanger, the gas cooling tower and the water scrubber into contact with the microbial catalyst to generate an organic substance.

[15] The apparatus for producing an organic substance according to [14], in which the organic substance generation portion brings the synthesis gas that has passed through the heat exchanger, the gas cooling tower, the filtration-type dust collector and the water scrubber in this order into contact with the microbial catalyst to generate an organic substance.

[16] The apparatus for producing an organic substance according to [14] or [15], in which the synthesis gas is cooled to 40° C. or lower with the water scrubber.

[17] The apparatus for producing an organic substance according to any one of [10] to [16], further including a distillation device that distills the organic substance, in which the distillation device uses a heat energy obtained from the synthesis gas with the heat exchanger for distillation.

[18] The apparatus for producing an organic substance according to any one of [10] to [17], in which the organic substance contains ethanol.

Advantageous Effects of Invention

According to the present invention, it becomes possible to provide a method for producing an organic substance and an apparatus for producing an organic substance that are capable of efficiently cooling a synthesis gas and converting the synthesis gas to an organic substance at a high conversion efficiency using a microbial catalyst.

BRIEF DESCRIPTION OF THE DRAWING

FIG. 1 is a schematic view showing the overall configuration of an apparatus for producing an organic substance according to an embodiment of the present invention.

DESCRIPTION OF EMBODIMENTS

The present invention will be described using an embodiment with reference to a drawing.

FIG. 1 shows an apparatus for producing an organic substance according to the embodiment of the present invention. Hereinafter, the apparatus for producing an organic substance and a method for producing an organic substance according to the embodiment of the present invention will be described in detail with reference to the embodiment.

An apparatus for producing an organic substance 1 includes a gasifier 2 that gasifies waste to generate a synthesis gas G1, a treatment unit 3 that carries out a treatment including at least a purification treatment on the synthesis gas G1 discharged from the gasifier 2 and an organic substance generation portion 30 that generates an organic substance by bringing a synthesis gas obtained by the treatment of the treatment unit 3 (hereinafter, also referred to as "purified synthesis gas G2") into contact with a microbial catalyst.

(Gasifier)

The waste that is gasified by the gasifier 2 may be industrial waste such as industrial solid waste or may be general waste such as municipal solid waste (MSW), and examples thereof include combustible substances such as plastic waste, raw garbage, discarded tires, biomass waste, food waste, building materials, wood, wooden chips, fibers and paper. Among these, municipal solid waste (MSW) is preferable.

The gasifier 2 includes a gasification furnace 10 and a reforming furnace 11. The gasification furnace 10 is not particularly limited, and examples thereof include a kiln gasification furnace, a fixed-bed gasification furnace, a fluidized-bed gasification furnace and the like. Into the gasification furnace 10, not only waste but also oxygen or an air and, furthermore, water vapor, if necessary, are injected. In the gasification furnace 10, the waste is heated at, for example, 500° C. to 700° C. and thereby thermally decomposed and partially oxidized as appropriate to be gasified. The thermally decomposed gas contains not only carbon monoxide and hydrogen but also gaseous tar, powdery char or the like. The thermally decomposed gas is supplied to the reforming furnace 11. A solid matter or the like that is generated as an impurity in the gasification furnace 10 is recovered as appropriate.

In the reforming furnace 11, the thermally decomposed gas obtained in the gasifier 2 is reformed, and the synthesis gas G1 is obtained. In the reforming furnace 11, the content rate of at least any of hydrogen and carbon monoxide in the thermally decomposed gas increases, and the thermally decomposed gas is discharged as the synthesis gas G1. In the reforming furnace 11, for example, tar, char or the like that is contained in the thermally decomposed gas is reformed into hydrogen, carbon monoxide or the like.

The temperature of the synthesis gas G1 in the reforming furnace 11 is not particularly limited, but is, for example, 900° C. or higher, preferably 900° C. or higher and 1300° C. or lower and more preferably 1000° C. or higher and 1200° C. or lower. When the temperature in the reforming furnace 11 is set within the above-described range, it becomes easy to obtain the synthesis gas G1 in which the content rates of carbon monoxide and hydrogen are high.

The temperature of the synthesis gas G1 that is discharged from the reforming furnace 11 (that is, gasifier 2) is the same as the temperature of the synthesis gas G1 and is, for example, 900° C. or higher, preferably 900° C. or higher and 1300° C. or lower and more preferably 1000° C. or higher and 1200° C. or lower.

The synthesis gas G1 that is discharged from the reforming furnace 11 (that is, gasifier 2) contains carbon monoxide and hydrogen. In addition, the synthesis gas G1 contains, for example, 0.1 vol % or more and 80 vol % or less of carbon monoxide and 0.1 vol % or more and 80 vol % or less of hydrogen.

The carbon monoxide concentration in the synthesis gas G1 is preferably 10 vol % or more and 70 vol % or less and more preferably 20 vol % or more and 55 vol % or less. In addition, the hydrogen concentration in the synthesis gas G1 is preferably 10 vol % or more and 70 vol % or less and more preferably 20 vol % or more and 55 vol % or less.

The synthesis gas G1 may contain, in addition to hydrogen and carbon monoxide, carbon dioxide, nitrogen, oxygen and the like. The carbon dioxide concentration in the synthesis gas G1 is not particularly limited, but is preferably 0.1 vol % or more and 40 vol % or less and more preferably 0.3 vol % or more and 30 vol % or less. In the case of generating ethanol using a microbial catalyst, it is particularly preferable to decrease the carbon dioxide concentration, and, from such a viewpoint, the carbon dioxide concentration is more preferably 0.5 vol % or more and 25 vol % or less.

The nitrogen concentration in the synthesis gas G1 is ordinarily 40 vol % or less and preferably 1 vol % or more and 20 vol % or less.

In addition, the oxygen concentration in the synthesis gas G1 is ordinarily 5 vol % or less and preferably 1 vol % or less. In addition, the oxygen concentration is preferably as low as possible as long as the oxygen concentration is 0 vol % or more. However, ordinarily, oxygen is inevitably contained in many cases, and the oxygen concentration is practically 0.01 vol % or more.

The concentrations of carbon monoxide, carbon dioxide, hydrogen, nitrogen and oxygen in the synthesis gas G1 can be set within predetermined ranges by appropriately changing combustion conditions such as the kind of the waste, the temperatures of the gasification furnace 10 and the reforming furnace 11 and the oxygen concentration of a supply gas that is supplied to the gasification furnace 11. For example, in a case where there is a desire to change the carbon monoxide or hydrogen concentration, the waste is changed to waste in which the rate of hydrocarbon (carbon and hydrogen) is high such as plastic waste, and, in a case where there is a desire to decrease the nitrogen concentration, a gas having a high oxygen concentration in the gasification furnace 10 is supplied.

Furthermore, in the synthesis gas G1, the concentration of each component such as carbon monoxide, carbon dioxide, hydrogen and nitrogen may be appropriately adjusted. The concentration is preferably adjusted by adding at least one of these components to the synthesis gas G1.

The volume percentage of each substance in the synthesis gas G1 described above means the volume percentage of each substance in the synthesis gas G1 that is discharged from the gasifier 2.

In the above description, an aspect in which the gasifier 2 includes the gasification furnace 10 and the reforming furnace 11 has been described, but the configuration of the gasifier 2 is not limited thereto, and the gasifier 2 may be a device in which a gasification furnace and a reforming furnace are integrated together or may be a gasifier of any type as long as the synthesis gas G1 can be generated.

(Treatment Unit)

The treatment unit 3 in the present embodiment includes at least a heat exchanger 20 and a gas cooling tower 21 as shown in FIG. 1. The treatment unit 3 further includes a filtration-type dust collector 22 in the post-stage of the gas cooling tower 21. The treatment unit 3 further includes a water scrubber 23 in the post-stage of the gas cooling tower 21.

In the present specification, "the post-stage" means the post-stage along the supply flow of gas of the synthesis gas G1. In addition, "the pre-stage" means the pre-stage along the supply flow of the synthesis gas G1. The supply flow of the synthesis gas G1 means the flow of the synthesis gas G1 while the synthesis gas G1 is discharged from the gasifier 2 and introduced into the organic substance generation portion 30.

<Heat Exchanger>

The synthesis gas G1 discharged from the gasifier 2 passes through the heat exchanger 20. The heat exchanger 20 is a device that cools the synthesis gas G1 using a heat medium. The heat exchanger 20 cools the synthesis gas G1 by transferring the heat energy of the synthesis gas G1 to the heat medium. As the heat exchanger 20, a boiler is preferably used. The boiler is a device in which water is communicated as a heat medium, and the communicated water is heated by the heat energy of the synthesis gas G1 and turned into vapor. When the boiler is used as the heat exchanger 20, it becomes possible to easily heat other devices with vapor generated from the boiler, and the heat energy of the synthesis gas G1 can be easily reused.

Here, the heat exchanger 20 to be used can be a device other than the boiler and may have any configuration as long as the heat energy is transferred to the heat medium from the synthesis gas G1, but a partition type in which the synthesis gas G1 and the heat medium do not come into direct contact with each other is preferable. The heat medium may be any of gas or liquid and may be a heat medium accompanying a phase change between gas and liquid. In addition, the heat energy from the synthesis gas G1 may be transferred to the heat medium in a state of having passed through a path with any shape such as a tubular shape or a plate shape.

The temperature of the synthesis gas G1 discharged from the gasifier 2 becomes as high as, for example 900° C. or higher as described above. Therefore, when cooled with the heat exchanger 20, the synthesis gas G1 is supplied to the gas cooling tower 21 at a relatively low temperature, which makes it possible to prevent the synthesis gas G1 from being excessively cooled in the gas cooling tower 21. Therefore, it is possible to decrease the amount of water that is sprayed to the synthesis gas G1 in the gas cooling tower 21, and furthermore, it becomes unnecessary to supply the synthesis gas G1 having a high water content rate to the filtration-type dust collector 22 and the water scrubber 23. Therefore, it is possible to suppress the amount of water transferred to the water scrubber 23 from the gas cooling tower 21 and to prevent water from excessively agglomerating in the filtration-type dust collector 22.

As described above, the heat exchanger 20 cools the synthesis gas G1 supplied at a high temperature of, for example, 900° C. or higher to a temperature of, for example, 200° C. or higher and 300° C. or lower and preferably 240° C. or higher and 280° C. or lower and supplies the synthesis gas G1 to the gas cooling tower 21. When the synthesis gas G1 is cooled to 200° C. or higher, it is possible to prevent the synthesis gas G1 the precipitation of an impurity, and, when the synthesis gas G1 is set to 240° C. or higher, it is possible to effectively prevent the precipitation of a tar component. When waste is gasified, the synthesis gas G1 contains a large amount of a tar component, but clogging by the tar component in the heat exchanger 20 can be prevented by preventing the precipitation of the tar component. In addition, when the synthesis gas G1 is set to 300° C. or lower, it becomes unnecessary to excessively cool the synthesis gas G1 in the gas cooling tower 21.

<Gas Cooling Tower>

The gas cooling tower 21 is a facility that cools a gas that passes through the inside of the gas cooling tower 21 (synthesis gas G1) by water spray. The gas cooling tower 21 includes one or more water spray openings 24 for spraying water to the synthesis gas G1 on the inner peripheral surface. Two or more water spray openings 24 are preferably provided, and the two or more water spray openings 24 are more preferably provided at different height positions in the cooling tower 21. When a plurality of the water spray openings 24 is provided and, furthermore, the height positions thereof are different, it is possible to more sufficiently and efficiently cool the synthesis gas G1 by water spray.

In the gas cooling tower 21, it is preferable that the synthesis gas G1 is introduced from the upper portion side, the synthesis gas G1 is passed through the inside of the gas cooling tower 21 so as to form a descending current, and the synthesis gas G1 is cooled by water sprayed from the water spray openings 24 while passing through the inside of the gas cooling tower 21. In this case, the synthesis gas G1 is preferably discharged from the lower portion side of the gas cooling tower 21.

The temperature of the synthesis gas G1 that is introduced into the gas cooling tower 21 is sufficiently higher than 100° C., but the water that is sprayed from the water spray openings 24 is lower than 100° C. Therefore, the synthesis gas G1 is cooled due to the temperature difference and is also cooled by the vaporization heat generated when the water sprayed from the water spray openings 24 vaporizes. A part of the vaporized water is preferably mixed into the synthesis gas G1. A part or all of the water that is sprayed from the water spray openings 24 may be in a vaporized state when sprayed.

In the gas cooling tower 21, the synthesis gas G1 is preferably cooled to a temperature of 100° C. or higher and 200° C. or lower and preferably discharged to the outside of the gas cooling tower 21 within the above-described temperature range. When the synthesis gas G1 is cooled to 200° C. or lower, it is possible to purify the synthesis gas G1 in the filtration-type dust collector 22 to be described below without damaging the filtration-type dust collector 22 or degrading the dust collection performance. In addition, when the synthesis gas G1 is cooled to 100° C. or higher, the majority of the sprayed water is vaporized and mixed into the synthesis gas G1. Therefore, in the gas cooling tower 21, since a large amount of the sprayed water is not discharged, there is no need to introduce a large drain facility into the gas cooling tower 21.

Here, a part of water sprayed to the gas cooling tower 21 may drop downward in the gas cooling tower 21 as a liquid and be recovered. In addition, an impurity, such as char or tar, in the synthesis gas G1 may also collide with the sprayed water and be thereby dropped downward and recovered.

In the gas cooling tower 21, it is preferable that the synthesis gas G1 is cooled to a temperature of more preferably 120° C. or higher and 180° C. or lower and still more preferably 130° C. or higher and 170° C. or lower, cooled to these temperatures and discharged to the outside. When the synthesis gas G1 is cooled to 120° C. or higher, it is possible to prevent the water mixed into the synthesis gas G1 from liquefying in a large quantity in the gas cooling tower 21 and, furthermore, the filtration-type dust collector 22 to be described below. In addition, when the synthesis gas G1 is cooled to 180° C. or lower, it becomes easy to further avoid the damage or function degradation of the filtration-type dust collector 22.

<Filtration-Type Dust Collector>

The synthesis gas G1 cooled in the gas cooling tower 21 passes through the filtration-type dust collector 22. As the filtration-type dust collector 22, a dust collector called a so-called bag filter can be used, and the bag filter includes a casing and a filter medium accommodated in the casing. The filter medium is not particularly limited, and, for example, woven fabric such as a glass fiber and a PTFE fiber, felt or the like is used.

The synthesis gas G1 contains a large amount of a solid impurity such as tar or char, but the solid impurity is removed when the synthesis gas G1 passes through the filtration-type dust collector 22. When the solid impurity is removed, it is possible to prevent the sticking of the solid impurity in each device in the post-stage of the filtration-type dust collector 22. For example, in the organic substance generation portion 30, it is ordinary that gas is blown into a reactor through a sparger, and the sticking of the solid impurity in the sparger can be prevented. Furthermore, when the solid impurity is removed, it is easy to enhance the activity of the microbial catalyst in the organic substance generation portion 30, and it is possible to prevent the death of the microbial catalyst due to the influence of the impurity and to synthesize an organic substance at a high conversion efficiency.

In the present specification, "remove" means that the concentration of a target substance to be removed in the gas is reduced by removing at least a part of the target substance from the synthesis gas and is not limited to the complete removing of the target substance to be removed.

When the synthesis gas G1 is cooled in the gas cooling tower 21 as described above, the temperature of the synthesis gas G1 at the time of passing through the filtration-type dust collector 22 also becomes a temperature of preferably 100° C. or higher and 200° C. or lower, more preferably 120° C. or higher and 180° C. or lower and still more preferably 130° C. or higher and 170° C. or lower. Therefore, it is possible to prevent the high-temperature synthesis gas G1 from damaging the filtration-type dust collector 22 or degrading the filtration performance. In addition, it is also possible to prevent the synthesis gas G1 that is contained in the synthesis gas G1 from liquefying in a large quantity in the filtration-type dust collector 22.

<Water Scrubber>

The synthesis gas G1 cooled in the gas cooling tower 21 passes through the water scrubber 23. In the present embodiment, the synthesis gas G1 cooled in the gas cooling tower 21 and discharged from the filtration-type dust collector 22 passes through the water scrubber 23 that is disposed in the post-stage of the filtration-type dust collector 22. The synthesis gas G1 contains a variety of impurities other than the above-described solid impurity, and, for example, a water-soluble impurity is contained. Examples of the water-soluble impurity include acidic gases such as hydrogen sulfide, hydrogen chloride and blue acid, basic gases such as ammonia and oxides such as NOx and SOx. These water-soluble impurities are removed when passing through the water scrubber 23.

In addition, the synthesis gas G1 also contains oil-based impurities such as BTEX (benzene, toluene, ethylbenzene and xylene), naphthalene, 1-naphthol and 2-naphthol, but these may also be removed appropriately in the water scrubber 23, and the solid impurity or the like that could not be recovered in the filtration-type dust collector 22 may also be appropriately removed.

The water scrubber 23 is not particularly limited as long as the water scrubber 23 is configured to bring the synthesis gas G1 and water into contact with each other and is, for example shown in FIG. 1, preferably configured to bring water sprayed from a nozzle 25 provided in the upper portion (for convenience, also referred to as "washing water") into contact with the synthesis gas G1. In this case, the water scrubber 23 is preferably provided with an introduction path 27, a supply path 28, a discharge path 29 and the like. In addition, a storage portion 26 that stores the washing water is provided in the lower portion of the water scrubber 23. The washing water stored in the storage portion 26 may be appropriately stirred with a stirring device, not shown.

The introduction path 27 is a path for introducing the synthesis gas G1 into the water scrubber 23, and an introduction opening 27A of the introduction path 27 is provided, for example, above the liquid surface of the washing water stored in the storage portion 26 in the water scrubber 23.

The supply path 28 supplies the washing water such that the water is circulated in the water scrubber 23 and brought into contact with the synthesis gas G1. Specifically, the supply path 28 makes the washing water stored in the storage portion 26 spray downward in the water scrubber 23 from the nozzle 25 to come into contact with the synthesis gas G1. Here, for example, a pump (not shown) is provided in the supply path 28, and the washing water is pneumatically sent to the nozzle 25 by the pump. In addition, the washing water is sprayed downward from the nozzle 25 in the water scrubber 23. The discharge path 29 is provided in the upper portion of the water scrubber 23 and discharges the synthesis gas G1 that has come into contact with the washing water sprayed from the nozzle 25 to the outside.

The washing water that is used in the water scrubber 23 may be water alone or a chemical may be added thereto as appropriate.

Furthermore, a removal device 19 may be provided in the water scrubber 23. The removal device 19 is a device for removing, for example, the impurities that are contained in the washing water (the oil-based impurities, the solid impurity, the water-soluble impurities and the like). The removal device 19 is preferably provided on a circulation path that circulates the water in the storage portion 26, for example. The removal device 19 preferably removes, for example, the oil-based impurities that are contained in the washing water, the solid impurity that does not dissolve in the washing water, the water-soluble impurities that dissolve in the washing water and the like. Therefore, the removal device 19 may be an oil-water separator or the like, may be a filter or the like that removes the solid impurity, may be a combination of two or more of these and may have any configuration as long as the impurities that are contained in the washing water can be removed. With providing the removal device 19, the water scrubber 23 prevents the accumulation of the impurities in the washing water.

The synthesis gas G1 is preferably cooled by coming into contact with water in the water scrubber 23. As described above, the synthesis gas G1 is cooled in the gas cooling tower 21 and introduced into the water scrubber 23 in a state of being cooled to a predetermined temperature (a temperature of preferably 100° C. or higher and 200° C. or lower, more preferably 120° C. or higher and 180° C. or lower and still more preferably 130° C. or higher and 170° C. or lower).

Incidentally, the temperature of the water that comes into contact with the synthesis gas G1 in the water scrubber 23 is lower than 100° C., preferably 0° C. or higher and 40° C. or lower and more preferably 5° C. or higher and 30° C. or lower.

As "the temperature of the water that comes into contact with the synthesis gas G1" in the present specification, in a case where the washing water is circulated and brought into contact with the synthesis gas G1 as described above, the temperature of the water immediately before coming into contact with the synthesis gas G1, that is, the water (washing water) sprayed from the nozzle 25 may be measured. In addition, in a case where the synthesis gas G1 is introduced into the stored water (washing water) as described below, the temperature of the washing water stored in the storage portion 26 may be measured.

The synthesis gas G1 comes into contact with the water having the above-described temperature in the water scrubber 23 and is thereby cooled to a temperature of, for example, lower than 100° C., preferably 40° C. or lower and more preferably 38° C. or lower. When the synthesis gas G1 is cooled to a predetermined temperature that is lower than the boiling point of water in the water scrubber 23 as described above, at least a part of water mixed into the synthesis gas G1 in the gas cooling tower 22 (water vapor) is condensed and removed. Therefore, it becomes possible to appropriately remove water even without separately providing a large device for removing the water mixed in the gas cooling tower 22. In addition, the synthesis gas G1 is cooled to 40° C. or lower, it is possible to supply the synthesis gas G1 having an appropriate temperature to the organic substance generation portion even without separately providing a cooling device. In addition, even in a case where a cooling device is included in a treatment device that is provided in the post-stage of the water scrubber 23, it is possible to reduce the load in the cooling device.

The synthesis gas G1 is preferably cooled to a temperature of, for example, 0° C. or higher by coming into contact with water and is preferably cooled to a temperature of 5° C. or higher.

It is preferable that the water scrubber 23 is provided with a temperature controller, not shown, and the temperature of the washing water is controlled with the temperature controller. The temperature controller may be attached to, for example, the supply path 28 to adjust the temperature of the washing water that passes through the inside of the supply path 28 or may be provided on the outer periphery of the water scrubber to adjust the temperature of the washing water stored in the storage portion 26 in the water scrubber. The temperature controller preferably puts the temperature of the washing water that passes through the supply path 28 or the washing water stored in the storage portion 26 into the above-described range by cooling or the like. In addition, the temperature of the water that is brought into contact with the synthesis gas G1 may be maintained within a certain temperature range by appropriately replacing the water that is stored in the storage portion 26.

In the above description, an aspect in which the synthesis gas G1 comes into contact with the washing water that is sprayed from the nozzle 25 in the water scrubber 23 has been described, but the synthesis gas G1 may be introduced into the washing water that is stored in the storage portion 26.

In this case, the supply path 28 and the nozzle 25 are not provided, and the washing water is not sprayed from the nozzle. In addition, the introduction opening 27A of the introduction path 27 is disposed below the liquid surface of the washing water stored in the storage portion 26. The synthesis gas G1 comes into contact with the washing water stored in the storage portion 26, whereby the synthesis gas G1 is washed and preferably cooled.

Even in a case where the synthesis gas G1 is introduced into the washing water that is stored in the storage portion 26, the temperature of the water that comes into contact with the synthesis gas G1 or the temperature of the synthesis gas G1 (that is, the temperature of the synthesis gas G1 that is introduced into the water scrubber 23 or the temperature of the cooled synthesis gas G1) is as described above.

(Other Treatment Devices)

The treatment unit 3 may have a treatment device other than the heat exchanger 20, the gas cooling tower 21, the filtration-type dust collector 22 and the water scrubber 23. As such treatment devices, a treatment device (also referred to as "post-stage treatment device") may be provided in the post-stage of the water scrubber 23, and the purified synthesis gas G2 that has passed through the water scrubber 23 may be supplied to the organic substance generation portion 30 after being appropriately treated with the post-stage treatment device.

Examples of the post-stage treatment device include a moisture separator including a gas chiller or the like, a low-temperature separation type (deep cooling type) separator, a fine particle separator composed of a variety of filters, a desulfurization device (sulfide separator), a film separation type separator, a deoxidation device, a pressure swing adsorption type separator (PSA), a temperature swing adsorption type separator (TSA), a pressure/temperature swing adsorption type separator (PTSA), a separator in which activated carbon is used, a deoxidation catalyst, specifically, a separator in which a copper catalyst or a palladium catalyst is used, and the like. One of these may be used singly or two or more may be jointly used.

The purified synthesis gas G2 discharged from the water scrubber 23 may be further purified with these post-stage treatment devices.

(Organic Substance Generation Portion)

As described above, the synthesis gas G1 that has passed through at least the heat exchanger 20 and the gas cooling tower 21 is supplied to the organic substance generation portion 30 as the purified synthesis gas G2. The purified synthesis gas G2 that is supplied to the organic substance generation portion 30 is preferably the purified synthesis gas G2 that has passed through the heat exchanger 20, the gas cooling tower 21, the filtration-type dust collector 22 and the water scrubber 23 in this order. In the organic substance generation portion 30, the purified synthesis gas G2 is brought into contact with the microbial catalyst to generate an organic substance. As the microbial catalyst, a gas-assimilating microbial is preferably used.

The organic substance generation portion 30 includes a fermenter (reactor) filled with a culture containing water and the microbial catalyst. The purified synthesis gas G2 is supplied to the inside of the fermenter, and the purified synthesis gas G2 is converted to an organic substance in the fermenter. The organic substance preferably contains ethanol.

As the fermenter, a continuous fermenting device is preferably used, and any of a stirring type, an air lift type, a cell tower type, a loop type, an open bond type and a photobio type may be used.

The purified synthesis gas G2 and the culture may be continuously supplied to the fermenter, but there is no need to supply the purified synthesis gas G2 and the culture at the same time, and the purified synthesis gas G2 may be supplied to the fermenter to which the culture has been supplied in advance. Ordinarily, the purified synthesis gas G2 is blown into the fermenter through a sparger or the like.

A culture medium that is used when the microbial catalyst is cultured is not particularly limited as long as the composition is appropriate depending on germs and is a liquid containing water, which is a main component, and nutrients (for example, vitamins, phosphoric acid and the like) dissolved or distributed in this water.

In the organic substance generation portion 30, an organic substance is generated due to the microbial fermentation of the microbial catalyst and an organic substance-containing liquid is obtained.

The temperature of the fermenter is preferably controlled to 40° C. or lower. When the temperature of the fermenter is controlled to 40° C. or lower, the microbial catalyst in the fermenter does not die, and the purified synthesis gas G2 comes into contact with the microbial catalyst, whereby an organic substance such as ethanol is efficiently generated.

The temperature of the fermenter is more preferably 38° C. or lower. In addition, in order to enhance the catalytic activity, the temperature is preferably 10° C. or higher, more preferably 20° C. or higher and still more preferably 30° C. or higher.

(Separator)

The apparatus for producing an organic substance 1 includes a separator 31 that separates at least water from the organic substance-containing liquid.

As the separator 31, a distillation device 33 is preferably included, and a solid-liquid separator 32 is more preferably included in the pre-stage of the distillation device 33. As the separator 31, the solid-liquid separator 32 and the distillation device 33 are preferably used in combination. Hereinafter, a separation step that is carried out by combining the solid-liquid separator 32 and the distillation device 33 will be specifically described.

<Solid-Liquid Separator>

The organic substance-containing liquid obtained in the organic substance generation portion 30 is preferably separated into a solid component mainly containing a microbial and a liquid component containing the organic substance in the solid-liquid separator 32. The organic substance-containing liquid obtained in the organic substance generation portion 30 contains, in addition to the organic substance, which is a target substance, the microbial that was contained in the fermenter, the carcass thereof or the like and is thus separated into solid and liquid to remove these. As the solid-liquid separator 32, there are a filter, a centrifuge, devices in which a solution precipitation method is used and the like. In addition, the solid-liquid separator 32 may be a device that separates the liquid component containing the organic substance from the solid component by evaporating the liquid component from the organic substance-containing liquid (for example, a heated-air dryer). At this case, the liquid component containing the organic substance, which is the target substance, may be fully evaporated or the liquid component may be partially evaporated such that the organic substance, which is the target, is preferentially evaporated.

<Distillation Device>

The distillation device 33 carries out distillation for separating the organic substance, which is the target substance. The distillation device 33 is capable of purifying a large amount of the organic substance in high purity with simple operation by means of separation by distillation. In the separation step that is carried out with the distillation device 33 in combination with the solid-liquid separator 32, distillation for further separating the organic substance, which is the target substance, from a liquid component separated with the solid-liquid separator 32 is carried out in the distillation device 33, whereby a large amount of the organic substance can be purified to a higher purity.

As the distillation device 33, a well-known distillation tower can be used. In addition, the distillation needs to be operated such that, for example, the organic substance, which is the target substance, (for example, ethanol) is contained in the distillate at a high purity and water is contained in the bottom product (that is, the distillation residue) as a main component (for example, 70 mass % or more and preferably 90 mass % or more). Such operation makes it possible to generally separate the organic substance, which is the target substance, and water.

The temperature in the distillation device 33 at the time of the distillation of the organic substance (for example, ethanol) is not particularly limited, but is preferably 100° C. or lower and more preferably approximately 70° C. to 95° C. When the temperature in the distillation device 33 is set within the above-described range, it is possible to reliably separate the required organic substance and the other components such as water.

The pressure in the distillation device 33 at the time of the distillation of the organic substance may be a normal pressure, but is preferably lower than the atmospheric pressure and more preferably approximately 60 to 150 kPa (gauge pressure). When the pressure in the distillation device 33 is set within the above-described range, it is possible to improve the separation efficiency of the organic substance and to improve the yield of the organic substance.

In the distillation device 33, the heat energy obtained from the synthesis gas G1 with the above-described heat exchanger 20 is preferably used for distillation. When the heat energy obtained from the synthesis gas G1 in the heat exchanger 20 is reused in the distillation device 33, it is possible to increase the temperature in the distillation device 33 at the time of the distillation of the organic substance. When the heat energy obtained from the synthesis gas G1 in the heat exchanger 20 is reused in the distillation device 33, it is possible to reduce the amount of energy used in the entire production process of the organic substance. The heat energy obtained from the synthesis gas G1 in the heat exchanger 20 can be transmitted through a heat energy path 33*a* connected to the heat exchanger 20 and the distillation device 33. The heat energy path 33*a* is not particularly limited and may have any configuration by which the heat energy of the synthesis gas G1 is transferred from the heat exchanger 20 to the distillation device 33 with the heat medium. The heat medium may be any of gas or liquid and may be a heat medium accompanying a phase change between gas and liquid. In addition, as described above, the heat exchanger 20 is preferably a boiler, and thus the heat medium is preferably water vapor. The use of water vapor as the heat medium makes it easy to reuse the heat energy of the synthesis gas G1. In a case where water vapor is used as the heat medium, a part of water vapor may be liquefied.

The water separated in the separator 31 is preferably reused and more preferably supplied to the gas cooling tower 21 and used for water spray in the gas cooling tower 21. When the water is reused as described above, the water that became unnecessary in the organic substance generation portion 30 does not become drainage water, which is preferable from the viewpoint of the environmental protection and the viewpoint of the economic efficiency. In addition, in the apparatus for producing an organic substance 1, the separator 31 and the gas cooling tower 21 may be connected to each other and a supply path 31*a* that supplies the water obtained in the separator 31 to the gas cooling tower 21 may be provided. The supply path 31*a* is not particularly limited, but is preferably made of a pipe or the like. In addition, the water separated in the separator 31 may be supplied to the gas cooling tower 21 after being further purified to have a higher purity.

As described above, according to the present embodiment, the synthesis gas G1 is cooled with the heat exchanger 20, and the synthesis gas G1 is cooled by water spray in the gas cooling tower 21, which makes it possible to cool the synthesis gas G1 without blowing nitrogen gas or an air. Therefore, it is possible to lower the temperature of the synthesis gas G1 without changing the composition of the synthesis gas G1, and it is possible to synthesize the organic substance without causing the death of the microbial catalyst.

In addition, according to the present embodiment, since the synthesis gas G1 is cooled by water spray in the gas cooling tower 21 after the synthesis gas G1 is cooled with the heat exchanger 20, the heat exchanger 20 plays a part of the role of cooling the synthesis gas G1, and the role of the gas cooling tower 21 for cooling is relieved. This makes it possible to reduce the amount of water sprayed to cool the synthesis gas G1 in the gas cooling tower 21 and, accordingly, to reduce the amount of drainage water from the gas cooling tower 21.

In addition, according to the present embodiment, it is possible to use the heat energy obtained from the synthesis gas G1 with the heat exchanger 20 to increase the temperature in the distillation device 33 at the time of the distillation of the organic substance. Therefore, it is possible to reduce the amount of energy that is procured from outside during the distillation with the distillation device 33 and to reduce the amount of energy used in the entire production process of the organic substance.

In the embodiment, a configuration in which the water scrubber 23 is provided has been described, but the water scrubber 23 may not be provided. In a case where the water scrubber 23 is not provided, the synthesis gas G1 that has passed through at least the gas cooling tower 21 and the filtration-type dust collector 22 is brought into contact with the microbial catalyst and converted to an organic substance in the organic substance generation portion 30. The synthesis gas G1 that is discharged from the filtration-type dust collector 22 in the present embodiment typically has a relatively high temperature (for example, 100° C. or higher), and, in a case where the water scrubber 23 is not provided, a cooling device other than the water scrubber 23 may be provided in the post-stage of the filtration-type dust collector 22, and the synthesis gas G1 discharged from the filtration-type dust collector 22 may be cooled with the cooling device other than the water scrubber 23.

In addition, in a case where the water scrubber 23 is not provided, not only the cooling device but also one or more treatment devices selected from the above-described post-stage treatment devices may be provided in the post-stage of the filtration-type dust collector 22, and the synthesis gas G1 discharged from the filtration-type dust collector 22 may be treated as appropriate with the post-stage treatment devices.

In addition, in a case where there is no need to purify the organic substance produced in the organic substance generation portion 30, a case where there is no need to separate water from the organic substance-containing liquid or the like, the separator 31 may not be provided.

In addition, in the embodiment, a configuration in which the filtration-type dust collector 22 is provided has been described, but the filtration-type dust collector 22 may not be provided. When the filtration-type dust collector 22 is not provided, the synthesis gas G1 cooled in the gas cooling tower 21 is supplied to the water scrubber 23 without passing through the filtration-type dust collector 22. For example, the filtration-type dust collector 22 may not be provided in a case where waste contains a small amount of a solid impurity or a case where a synthesis gas is produced using a raw material other than waste as described below. It is needless to say that both the water scrubber 23 and the filtration-type dust collector 22 may not be provided.

As described above, the treatment unit 3 in the apparatus for producing an organic substance includes at least the heat exchanger 20 and the gas cooling tower 21 and preferably further includes the filtration-type dust collector 22 and the water scrubber 23. In addition, the treatment unit 3 may additionally have the post-stage treatment devices or the like as appropriate. These have been described above in detail and thus will not be described again.

Furthermore, in the embodiment, an aspect in which the synthesis gas G1 is obtained from waste in the gasifier 2 has been described, but the synthesis gas G1 may be generated from a substance other than waste in the gasifier 2. For example, the synthesis gas G1 may be generated from fossil resources such as natural gas, coal, heavy oil, petroleum discharged gas and oil shale, biomass other than waste or the like. In addition, the synthesis gas G1 may be a gaseous by-product in a variety of production processes such as a steel production process, and, for example, the gasifier 2 may configure a steel production facility or the like.

REFERENCE SIGNS LIST

1 Device for producing organic substance
2 Gasifier
3 Treatment unit
10 Gasification furnace
11 Reforming furnace
20 Heat exchanger
21 Gas cooling tower
22 Filtration-type dust collector
23 Water scrubber
24 Water spray opening
25 Nozzle
26 Storage portion
27 Introduction path
28 Supply path
29 Discharge path
30 Organic substance generation portion
31 Separator
31a Supply path
32 Solid-liquid separator
33 Distillation device
33a Heat energy path
G1 Synthesis gas
G2 Purified synthesis gas

The invention claimed is:

1. An apparatus for producing an organic substance comprising:
a gasifier that generates a synthesis gas;
a heat exchanger through which the synthesis gas discharged from the gasifier is passed to be cooled;
a gas cooling tower through which the synthesis gas cooled in the heat exchanger is passed to be cooled by water spray;
an organic substance generation portion; and
a water scrubber which is disposed in a post-stage of the gas cooling tower and through which the synthesis gas cooled in the gas cooling tower is passed,
wherein the organic substance generation portion brings the synthesis gas that has passed through at least the heat exchanger, the gas cooling tower and the water scrubber into contact with the microbial catalyst to generate an organic substance.

2. The apparatus for producing an organic substance according to claim 1,
wherein a temperature of the synthesis gas discharged from the gasifier is 900° C. or higher.

3. The apparatus for producing an organic substance according to claim 1,
wherein the synthesis gas is cooled to a temperature of 200° C. or higher and 300° C. or lower in the heat exchanger.

4. The apparatus for producing an organic substance according to claim 1, further comprising:
a filtration dust collector which is disposed in a post-stage of the gas cooling tower and through which the synthesis gas cooled in the gas cooling tower is passed,
wherein the organic substance generation portion brings the synthesis gas that has passed through at least the heat exchanger, the gas cooling tower, the filtration dust collector, and the water scrubber into contact with the microbial catalyst to generate an organic substance.

5. The apparatus for producing an organic substance according to claim 1,
wherein the synthesis gas is cooled to 40° C. or lower with the water scrubber.

6. The apparatus for producing an organic substance according to claim 1, further comprising:
a distillation device that distills the organic substance,
wherein the distillation device uses a heat energy obtained from the synthesis gas with the heat exchanger for distillation.

7. The apparatus for producing an organic substance according to claim 1,
wherein the organic substance contains ethanol.

8. An apparatus for producing an organic substance comprising:
a gasifier that generates a synthesis gas;
a heat exchanger through which the synthesis gas discharged from the gasifier is passed to be cooled to a temperature of 200° C. or higher and 300° C. or lower;
a gas cooling tower through which the synthesis gas cooled in the heat exchanger is passed to be cooled by water spray to a temperature of 100° C. or higher and 200° C. or lower;
a water scrubber which is disposed in a post-stage of the gas cooling tower and through which the synthesis gas cooled in the gas cooling tower is passed; and
an organic substance generation portion that brings the synthesis gas that has passed through at least the heat exchanger, the gas cooling tower and the water scrubber into contact with a microbial catalyst to generate an organic substance.

9. The apparatus for producing an organic substance according to claim 8,
wherein the synthesis gas is cooled to 40° C. or lower with the water scrubber.

\* \* \* \* \*